(12) United States Patent
Andrensek et al.

(10) Patent No.: US 9,067,895 B2
(45) Date of Patent: Jun. 30, 2015

(54) PROCESSES FOR THE PREPARATION OF KEY INTERMEDIATE FOR THE SYNTHESIS OF ROSUVASTATIN OR PHARMACEUTICALLY ACCEPTABLE SALTS THEREOF

(75) Inventors: Samo Andrensek, Ljubljana (SI); Jolanda Anzel, Ljubljana (SI); Marjeta Hocevar, Ljubljana (SI); Zdenko Casar, Ljubljana (SI)

(73) Assignee: LEK PHARMACEUTICALS D.D., Ljubljana (SI)

(*) Notice: Subject to any disclaimer, the term of this patent is extended or adjusted under 35 U.S.C. 154(b) by 0 days.

(21) Appl. No.: 13/515,782

(22) PCT Filed: Dec. 15, 2010

(86) PCT No.: PCT/EP2010/069706
§ 371 (c)(1),
(2), (4) Date: Sep. 26, 2012

(87) PCT Pub. No.: WO2011/073232
PCT Pub. Date: Jun. 23, 2011

(65) Prior Publication Data
US 2013/0018065 A1   Jan. 17, 2013

(30) Foreign Application Priority Data
Dec. 16, 2009   (EP) .................................. 09179416

(51) Int. Cl.
*C07D 239/02* (2006.01)
*C07D 239/42* (2006.01)
*C07D 405/06* (2006.01)
*C07F 7/18* (2006.01)

(52) U.S. Cl.
CPC ............ *C07D 239/42* (2013.01); *C07D 405/06* (2013.01); *C07F 7/1856* (2013.01)

(58) Field of Classification Search
CPC .. C07D 239/42; C07D 405/06; A61K 31/505; A61K 31/506
USPC ........................................................ 544/297
See application file for complete search history.

(56) References Cited

FOREIGN PATENT DOCUMENTS

| EP | 2336116 A1 | * | 6/2011 |
|----|-----------|---|--------|
| WO | WO 0042024 A1 | * | 7/2000 |
| WO | WO 2005/042552 A1 | | 5/2005 |
| WO | WO 2006100689 A1 | * | 9/2006 |
| WO | WO 2006136407 A1 | * | 12/2006 |
| WO | WO 2007/039287 A1 | | 4/2007 |
| WO | WO 2008/119810 A2 | | 10/2008 |
| WO | WO 2008119810 A2 | * | 10/2008 |

OTHER PUBLICATIONS

N. G. Anderson, Practical Process & Research Development (2000).*
J.H. Poupaert, Drug Design: Basic Principles and Applications, in 2 Encyclopedia of Pharmaceutical Technology 1362-1369, 1367 (James Swarbrick ed., 3rd ed., 2007).*
R. Wilson et al., 71 Journal of Organic Chemistry 8329-8351, 8326 (2006).*
N.G. Anderson, Practical Process & Research Development 27-50 (2000).*
N. Anderson, 8 Organic Process Research & Development 260-286 (2004).*
H.-J. Federsel, 12 Organic Process Research & Development 512-521 (2008).*
Leonard et al., Advanced Practical Organic Chemistry 177-226 (2nd ed., 1985).*
Z. Časar et al., 75 Journal of Organic Chemistry 6681-6684 (Sep. 3, 2010).*

* cited by examiner

*Primary Examiner* — Alexander R Pagano
(74) *Attorney, Agent, or Firm* — Arent Fox LLP (57) ABSTRACT

The present invention relates in general to the field of organic chemistry and in particular to a process for the preparation of 5-((E)-2-((2S,4R)-4-hydroxy-6-oxotetrahydro-2H-pyran-2-yl)vinyl)-4-(4-fluorophenyl)-6-isopropyl-2-(N-methyl-methanesulfonylamino)pyrimidine (RSVL) as well as a process for preparing crystalline 5-((E)-2-((2S,4R)-4-(tert-butyldimethylsilyloxy)-6-oxotetrahydro-2H-pyran-2-yl)vinyl)-4-(4-fluorophenyl)-6-isopropyl-2-(N-methylmethanesulfonylamino)pyrimidine (RSVLTBS) useful as key intermediates for the preparation of rosuvastatin or pharmaceutically acceptable salts thereof.

6 Claims, 5 Drawing Sheets

PROCESSES FOR THE PREPARATION OF KEY INTERMEDIATE FOR THE SYNTHESIS OF ROSUVASTATIN OR PHARMACEUTICALLY ACCEPTABLE SALTS THEREOF

CROSS-REFERENCE TO RELATED APPLICATION

This application is a National Stage entry of International Application No. PCT/EP2010/069706, filed Dec. 15, 2010, which claims priority to European Application No. 09179416.4, filed Dec. 16, 2009, the entire specifications, claims and drawings of which are incorporated herewith by reference.

FIELD OF THE INVENTION

The present invention relates to a process for the preparation of 5-((E)-2-((2S,4R)-4-hydroxy-6-oxotetrahydro-2H-pyran-2-yl)vinyl)-4-(4-fluorophenyl)-6-isopropyl-2-(N-methylmethanesulfonyl amino)pyrimidine (RSVL) as well as a process for preparing crystalline 5-((E)-2-((2S,4R)-4-(tert-butyldimethylsilyloxy)-6-oxotetrahydro-2H-pyran-2-yl)vinyl)-4-(4-fluorophenyl)-6-isopropyl-2-(N-methylmethanesulfonylamino)pyrimidine (RSVLTBS) useful as key intermediates for the preparation of rosuvastatin or pharmaceutically acceptable salts thereof.

BACKGROUND OF THE INVENTION 5-((E)-2-((2S,4R)-4-hydroxy-6-oxotetrahydro-2H-pyran-2-yl)vinyl)-4-(4-fluorophenyl)-6-isopropyl-2-(N-methyl-methanesulfonylamino)pyrimidine (rosuvastatin lactone—RSVL) is a possible key intermediate in the synthesis of rosuvastatin and its pharmaceutically acceptable salts. Rosuvastatin calcium, chemically described as bis[(3R,5S,E)-7-(4-(4-fluorophenyl)-6-isopropyl-2-(N-methylmethylsulfonamido)pyrimidin-5-yl)-3,5-dihydroxyhept-6-enoic acid] calcium salt, is a synthetic lipid-lowering agent that acts as an inhibitor of 3-hydroxy-3-methylglutaryl-coenzyme A reductase (HMG-CoA reductase inhibitor). HMG-CoA reductase inhibitors are commonly referred to as "statins." Statins are therapeutically effective drugs used for reducing low density lipoprotein (LDL) particle concentration in the blood stream of patients at risk for cardiovascular disease. Therefore, rosuvastatin calcium is used in the treatment of hypercholesterolemia and mixed dyslipidemia.

Rosuvastatin and the synthesis of rosuvastatin calcium was first disclosed in EP 521471 A1; in the last two steps of the whole synthesis provided by hydrolysis of methyl ester of rosuvastatin (methyl rosuvastatin) in polar solvent, e.g. ethanol, in the presence of a base, following by isolation of sodium salt of rosuvastatin (sodium rosuvastatin) and converting said sodium salt of rosuvastatin with a water soluble calcium salt under aqueous conditions to calcium salt of rosuvastatin.

International patent application WO 2004/052867 A1 describes the preparation of rosuvastatin using rosuvastatin lactone as an intermediate. Rosuvastatin lactone is isolated from toluene solution by evaporation of solvent.

International patent application WO 2005/040134 A1 discloses rosuvastatin lactone as a precipitated solid from hexane and its use for preparation of amorphous rosuvastatin calcium via rosuvastatin lactone.

International applications WO 2007/039287 A1 and WO 2008/119810 A2 describe the synthesis of rosuvastatin via 5-((E)-2-(2S,4R)-4-(tert-butyldimethylsilyloxy)-6-oxotetrahydro-2H-pyran-2-yl)vinyl)-4-(4-fluorophenyl)-6-isopropyl-2-(N-methylmethanesulfonylamino) pyrimidine (RSVLTBS). RSVLTBS is isolated as a white amorphous solid.

The object of the present invention is to provide an improved process for preparing 5-((E)-2-((2S,4R)-4-hydroxy-6-oxotetrahydro-2H-pyran-2-yl)vinyl)-4-(4-fluorophenyl)-6-isopropyl-2-(N-methylmethanesulfonylamino) pyrimidine (rosuvastatin lactone—RSVL) and a process for preparing crystalline 5-((E)-2-((2S,4R)-4-(tert-butyldimethylsilyloxy)-6-oxotetrahydro-2H-pyran-2-yl)vinyl)-4-(4-fluorophenyl)-6-isopropyl-2-(N-methylmethanesulfonylamino)pyrimidine (RSVLTBS), so as to provide valuable intermediates for the preparation of rosuvastatin and pharmaceutically acceptable salts thereof.

SUMMARY OF THE INVENTION

The present invention provides the following items including main aspects and preferred embodiments, which respectively alone and in combination particularly contribute to solving the above object and eventually provide additional advantages:

1. A process for preparing the compound of formula RSVL comprising the steps of:
providing a compound of formula RSVLTBS:

converting the compound of formula RSVLTBS into the compound of formula RSVL by removal of silyl protection group and isolating said compound of formula RSVL.

2. The process according to item (1), wherein step of removal of silyl protection group is performed in the presence of tetrabutylammonium fluoride and acid in organic solvent, preferably said acid is acetic acid and preferably said solvent is tetrahydrofuran 3. The process according to any one of items (1)-(2), wherein RSVL is isolated as an oily product.
4. The process according to item (3), wherein said RSVL is further purified by extraction with ether, preferably methyl t-butyl ether is used.
5. The process according to any one of items (3)-(4) further comprising a step of crystallisation of RSVL from the solvent selected from the group consisting of alcohols, ethers and mixtures thereof, preferably solvent is selected from the group consisting of ethanol, 2-propanol and methyl t-butyl ether
6. The process according to any one of items (1)-(5), wherein said RSVLTBS is in crystalline form.
7. RSVLTBS in crystalline form.
8. RSVLTBS according to item (7) wherein said crystalline form is selected from the group consisting of:
    a) Form I, characterized by XRD pattern having any 6 peaks at 2θ values selected from the group consisting of: 5.1, 10.2, 12.5, 14.7, 15.3, 17.0, 17.7, 20.4, 26.6 and 30.8, respectively exactly or ±0.2 degrees 2θ at the indicated 2θ values and/or by
       having a melting point falling in a range of 85-105° C., and
    b) Form II, characterized by XRD pattern having any 6 peaks at 2θ values selected from the group consisting of 5.1, 12.4, 13.1, 14.3, 17.6, 18.9, 22.7, 24.2, 24.8 and 25.0, respectively exactly or ±0.2 degrees 2θ at the indicated 2θ values and/or by
       having a melting point falling in a range of 70-92° C.
9. A process for preparation of RSVLTBS in crystalline form according to any one of items (7) to (8) comprising a step of:
    a) adding organic solvent to RSVLTBS
    b) optionally heating the mixture of step a) to allow RSVLTBS to dissolve
    c) cooling the solution of step b)
    d) allowing the crystals of RSVLTB to crystallize subsequent to step c).
10. The process according to item (9) wherein organic solvent is selected from the group consisting of alkanes, alcohols, ethers, esters and mixtures thereof, preferably solvent is a mixture of n-butanol and $C_6$-$C_7$ n-alkane.
11. The process for purification of crude RSVL comprising a step of extraction of crude RSVL with ether.
12. A process according to item (11) wherein said ether is selected from the group consisting of diethyl ether, diisopropyl ether, methyl t-butyl ether, preferably methyl t-butyl ether is used.
13. The process for preparing RSVL in crystalline form comprising a step of crystallisation of crude RSVL from the solvent selected from the group consisting of alcohols, ethers and mixtures thereof.
14. The process according to item (13) wherein solvent is selected from the group consisting of ethanol, 2-propanol and methyl t-butyl ether.
15. Amorphous RSVL.
16. The process for purification of RSVLTBS using high performance liquid chromatography, wherein a stationary phase is selected from the group consisting of DIOL and $SiO_2$ and mobile phase is selected from the group consisting of mixture of n-alkane and alcohol and mixture of n-alkane, alcohol and water.
17. The process according to item (16) herein said n-alkane is selected from the group consisting of n-hexane and n-heptane.
18. The process according to any one of items (16)-(17) wherein said alcohol is linear alcohol, preferably $C_2$-$C_{12}$ linear alcohol, more preferably $C_2$-$C_8$ linear alcohol, most preferably n-butanol is used.
19. A process for the preparation of rosuvastatin or pharmaceutically acceptable salt thereof, comprising the steps of:
    a) carrying out a process for preparing the compound of formula RSVL according to any one of items (1)-(6) and (11)-(14) and
    b) subjecting the thus prepared compound of formula RSVL to further synthesis steps to yield rosuvastatin or pharmaceutically acceptable salts thereof.
20. A process for the preparation of a pharmaceutical composition comprising rosuvastatin as active ingredient, comprising the steps of:
    a) preparing rosuvastatin or pharmaceutically acceptable salts thereof according to the process according to item (19), and
    b) admixing the thus prepared rosuvastatin or pharmaceutically acceptable salt thereof with at least one pharmaceutically acceptable excipient.
21. A process for the preparation of rosuvastatin or pharmaceutically acceptable salt thereof, comprising the steps of:
    a) carrying out a process for preparing RSVLTBS according to any one of items (9)-(10), and (16)-(18),
    b) subjecting the thus prepared RSVLTBS to further synthesis steps to yield rosuvastatin or pharmaceutically acceptable salts thereof.
22. A process for the preparation of a pharmaceutical composition comprising rosuvastatin as active ingredient, comprising the steps of:
    a) preparing rosuvastatin or pharmaceutically acceptable salts thereof according to the process according to item (21), and
    b) admixing the thus prepared rosuvastatin or pharmaceutically acceptable salt thereof with at least one pharmaceutically acceptable excipient.
23. Use of RSVLTBS according to any one of items (7)-(8) for the synthesis of rosuvastatin or pharmaceutically acceptable salt thereof.

According to the present invention, it has been surprisingly found that a more efficient synthesis of rosuvastatin lactone (RSVL) can be carried out by selecting suitable starting material 5-((E)-2-((2S,4R)-4-(tert-butyldimethylsilyloxy)-6-oxotetrahydro-2H-pyran-2-yl)vinyl)-4-(4-fluorophenyl)-6-isopropyl-2-(N-methylmethanesulfonylamino)pyrimidine (RSVLTBS) which can be converted to the desired product in a simple manner. Moreover, the process for the preparation is more efficient as it allows beneficial reaction conditions providing for less byproducts and thus higher purity of the product and higher yields.

Furthermore according to present invention RSVLTBS in crystalline form is prepared. There is a need in the art for RSVLTBS in crystalline form as crystalline forms have better thermal stability, and offer advantages for preparing reproducible pharmaceutical formulations compared to amorphous and/or oily substances. Further, there is a need to provide RSVLTBS in crystalline form in an aimed and reproducible manner, thereby allowing to obtain RSVLTBS in crystalline form in good purity.

The present invention satisfies this need by providing RSVLTBS in crystalline form that is easy to handle and has a high degree of purity and by providing process for repeatedly obtaining said RSVLTBS in crystalline form.

As a result, desirable key intermediates for the preparation of rosuvastatin or pharmaceutically acceptable salts thereof are provided by a significantly improved process.

DETAILED DESCRIPTION OF THE INVENTION

The present invention is now described in more detail by referring to further preferred and further advantageous embodiments and examples, which are however presented for illustrative purposes only and shall not be understood as limiting the scope of the present invention.

According to one aspect of the present invention, the compound of formula 5-((E)-2-((2S,4R)-4-hydroxy-6-oxotetrahydro-2H-pyran-2-yl)vinyl)-4-(4-fluorophenyl)-6-isopropyl-2-(N-methylmethanesulfonylamino)pyrimidine (RSVL) is prepared by converting 5-((E)-2-((2S,4R)-4-(tert-butyldimethylsilyloxy)-6-oxotetrahydro-2H-pyran-2-yl)vinyl)-4-(4-fluorophenyl)-6-isopropyl-2-(N-methylmethanesulfonylamino)pyrimidine (RSVTBLS) by deprotection to compound RSVL as presented on the following scheme:

The reaction is performed in the presence of tetrabutylammonium fluoride and acid in organic solvent, preferably said acid is acetic acid and preferably said solvent is tetrahydrofuran. The reaction mixture is heated, preferably to a temperature of about 40° C. and stirred, preferably for a period of 10 to 24 hours, more preferably for a period of 15 to 22 hours. Subsequently solvent is evaporated and RSVL is isolated (for example as an oily product, preferably RSVL is isolated in a crystalline form).

According to another aspect of present invention said RSVL (for example isolated as an oily product) can be further purified by extraction. The oily RSVL is dissolved in appropriate solvent, preferably ether is used, most preferably methyl t-butyl ether. The solution is subsequently washed preferably with water and organic solvent is removed, preferably by evaporation and crystalline RSVL can be obtained.

Another aspect of present invention is a process for crystallisation of RSVL. Organic solvent is added to RSVL. Said organic solvent is selected from the group consisting of alcohols, ethers and mixtures thereof, more preferably solvent is selected from the group consisting of ethanol, 2-propanol and methyl t-butyl ether, most preferably solvent is 2-propanol. The mixture is subsequently heated to produce clear solution. Crystalline RSVL can be isolated or recovered from the reaction solution by precipitation. The precipitation can be spontaneous depending on solvent system. Alternatively, the precipitation can be induced by reducing the temperature of reaction mixture, especially if initial temperature of reaction mixture is elevated. The precipitation can also be induced by reduction of solution volume, preferably under diminished pressure, or by complete evaporation of solvent. Furthermore, the precipitation may be caused by adding an antisolvent, e.g. water. Said process of crystallisation can be repeated (recrystallisation) in order to further purify RSVL.

In one aspect of the invention the precipitation of crystalline RSVL occurs when said heated mixture is left to cool, preferably to room temperature, to give crystals of RSVL. Obtained crystals of RSVL may be separated by techniques well known in the art, e.g. filtration, centrifugation, decanting.

Thus, RSVL prepared from RSVLTBS according to the procedure of present invention is crystalline and of high purity (HPLC area % of 97 and higher) and exhibits melting point at about 130 to 145° C., preferably at about 135 to 141° C., and might be further characterized by XRD pattern comprising the following characteristic reflection angles at 2θ values of: 4.0, 7.9, 11.9, 14.7, 15.9, 19.6, 20.2, 21.0, 21.6 and 22.5 respectively exactly or ±0.2 degrees 2θ at the indicated 2θ values.

The RSVL prepared from RSVLTBS and further purified either by extraction and/or by crystallisation according to present invention can be obtained in high yields (85% and higher) and with high purity and is therefore suitable for use in further synthesis steps to obtain rosuvastatin that is less affected by critical byproducts.

Another aspect of present invention is amorphous RSVL and a process for its preparation. Amorphous RSVL can be prepared from a solvent selected from the group consisting of dry alcohol (preferably selected form the group consisting of methanol, ethanol and 2-propanol), ester (preferably ethyl acetate and/or methyl t-butyl ether), ether (preferably tetrahydrofuran and/or methyl t-butyl ether) and mixtures thereof. RSVL (crystalline or as an oily product) is dissolved in said solvent. Subsequently RSVL in an amorphous form may be recovered from the solution by spray drying. Alternatively, the RSVL in an amorphous from may be recovered from the solution by freeze-drying. The amorphous form of RSVL can also be recovered from the solution by adding a suitable additional solvent/second solvent resulting in the precipitation of the amorphous form and removing the solvent therefrom by filtration, filtration under vacuum, decantation or centrifugation. Thus, amorphous RSVL prepared according to present invention is of high purity and stable enough for the use in the preparation of rosuvastatin or pharmaceutically acceptable salts thereof.

Another aspect of present invention is RSVLTBS in crystalline form and a process for its preparation. Organic solvent is added to RSVLTBS. Solvent is selected from the group consisting of alkanes, alcohols, ethers, esters and mixtures thereof, preferably in a mixture of an alcohol and an alkane, in which the alcohol is a linear alcohol, preferably a $C_2$-$C_{12}$ linear alcohol, more preferably a $C_2$-$C_8$ linear alcohol, most preferably n-butanol, and the alkane is preferably $C_5$-$C_{10}$ linear alkane (n-alkane), more preferably $C_6$-$C_7$ linear alkane is used. The preferred mixture is n-butanol/heptane in a preferred assay of 1-50% (v/v) of n-butanol in $C_6$-$C_7$ linear alkane.

RSVLTBS may be dissolved in a solvent or mixture of solvents, optionally the mixture is heated to allow RSVLTBS to dissolve. In another embodiment RSVTBLS is dissolved in more polar phase and then diluted by alkane. The solution is optionally filtered. Crystalline RSVLTBS can be isolated or recovered from the reaction solution by precipitation. The precipitation can be spontaneous depending on solvent system. Alternatively, the precipitation can be induced by reducing the temperature of reaction mixture, especially if initial temperature of reaction mixture is elevated. The precipitation can also be induced by reduction of solution volume, preferably under diminished pressure, or by complete evaporation of solvent. Furthermore, the precipitation may be caused by adding an antisolvent, e.g. water or by enrichment of the solvent in which RSVTBLS is less soluble by evaporation of more volatile solvent in which is RSVLTBS more soluble. In one aspect of the invention the precipitation of crystalline RSVLTBS occurs when said heated mixture is left to cool, preferably to temperature below room temperature, more preferably to temperature below 10° C., to give crystals of RSVLTBS.

Obtained crystals of RSVLTBS may be separated by techniques well known in the art, e.g. filtration, centrifugation, decanting.

In the first, but not limiting example, oily RSVTBLS is dissolved in a mixture of 1 to 20% n-butanol in $C_6$-$C_7$ linear alkane at temperature around 20 to 30° C. The mixture is subsequently cooled to a temperature around −20 to +10° C., preferably to temperature around 0 to 5° C. Thus obtained crystalline RSVLTBS form I exhibits melting point at about 85 to 105° C., preferably at about 90 to 100° C., and might be further characterized by XRD pattern comprising the following characteristic reflection angles at 2θ values of: 5.1, 10.2, 12.5, 14.7, 15.3, 17.0, 17.7, 20.4, 26.6 and 30.8, respectively exactly or ±0.2 degrees 2θ at the indicated 2θ values (Form I).

In the second, but not limited example RSVTBLS is dissolved in a mixture of 10 to 50% n-butanol in $C_6$-$C_7$ linear alkane by heating, preferably to reflux temperature and than the mixture is cooled to a temperature around −20 to 10° C., preferably to a temperature below 0° C. Thus obtained crystalline RSVLTBS form II exhibits melting point at about 70 to 92° C., preferably at about 78 to 88° C., and might be further characterized by XRD pattern comprising the following characteristic reflection angles at 2θ values of: 5.1, 12.4, 13.1, 14.3, 17.6, 18.9, 22.7, 24.2, 24.8 and 25.0, respectively exactly or ±0.2 degrees 2θ at the indicated 2θ values° (Form II)

The fact that RSVLTBS according to present invention can be isolated as a crystalline material enables efficient purification of RSVLTBS. Isolation of crystalline RSVLTBS results in an enrichment of the main substance and in diminished level of impurities. For example when crystalline form I of RSVLTBS according to present invention is prepared the enrichment from 25-40 of HPLC area % to above 60 HPLC area % can be achieved. Furthermore the level of impurities can be significantly reduced (e.g. the level of RSVLTBS diastereoisomer impurity is reduced to below 20 HPLC area %) When crystalline form II of RSVLTBS according to present invention is prepared for example the enrichment from 65 HPLC area % to 90 HPLC area % can be achieved and the level of impurities can again be significantly reduced (e.g. the level of RSVLTBS diastereoisomer impurity can be reduced from 20 HPLC area % to 10 HPLC area % or even lower). Beneficially the process of crystallisation can be repeated and assays of more than 95 HPLC area % of RSVLTBS and less that 1 HPLC area % of RSVLTBS diastereoisomer impurity may be obtained. Preferably purification is performed via crystalline form II of RSVLTBS due to lower solvent volumes used.

Another aspect of invention is process for purification of RSVLTBS using high performance liquid chromatography. RSVLTBS, one of the most important key intermediates for rosuvastatin synthesis, may contain many impurities (e.g. optical isomers, Z-E isomers as well as cyclic isomer with 8 optical isomers) in different ratios which may consequentially influence the quality of the final rosuvastatin calcium. The RSVLTBS is effectively purified if stationary phase is selected from the group consisting of DIOL and $SiO_2$ and mobile phase is selected from the group consisting of mixture of n-alkane and alcohol and mixture of n-alkane, alcohol and water. Preferably said n-alkane is n-hexane or n-heptane and said linear alcohol is preferably $C_2$-$C_{12}$ linear alcohol, more preferably $C_2$-$C_8$ linear alcohol, most preferably n-butanol is used. RSVLTBS isolated by chromatographic elution was isolated by complete evaporation as an oily substance which may be crystallised according to the invention or by optional concentration and spontaneous precipitation from the eluting solution. Such product is of high purity (preferably having more than 95 HPLC area % of RSVLTBS and having less than 1 HPLC area % of diastereoisomer impurity).

Figure 8:
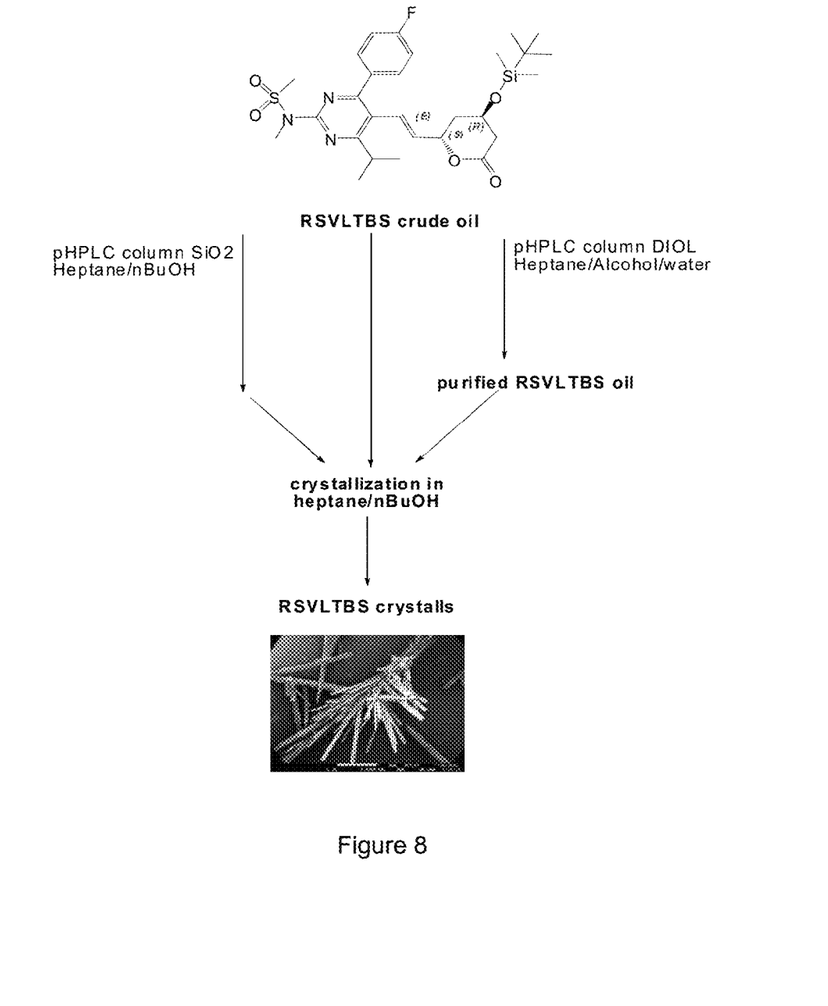
FIG. 8 shows a reaction scheme for preparing crystalline RSVLTBS according to example aspects of the invention.

Possible ways of preparing crystalline RSVLTBS according to various example aspects of the present invention are further presented in FIG. 8.

In a preferred aspect of the invention crystalline RSVL of high purity (preferably having more than 97 HPLC area % of RSVL) is prepared according to a process comprising the following steps:

a) converting crude oily RSVLTBS to crystalline RSVLTBS by treating crude oily RSVLTBS with a mixture of n-butanol and $C_6$-$C_7$ linear alkane b) recrystallizing the obtained RSVLTBS product to reach the purity of more than 95 HPLC area % of RSVLTBS and having less than 1 HPLC area % of RSVLTBS diastereoisomer impurity c) desilylating RSVLTBS to obtain crude RSVL d) treating RSVL by ethers to obtain crystalline product e) optionally recrystallizing the obtained product to obtain RSVL of high purity (preferably having more than 97 HPLC area % of RSVL).

In another preferred aspect of the invention crystalline RSVL of high purity (preferably having more than 97 HPLC area % of RSVL) is prepared according to a process comprising the following steps:

a) purifying crude oily RSVLTBS by column chromatography using DIOL or SiO$_2$ as a stationary phase and n-butanol and C$_6$-C$_7$ linear alkane mixture as a mobile phase b) evaporating mobile phase to obtain pure oily RSVLTBS c) crystallizing the obtained product by treating with n-butanol and C$_6$-C$_7$ linear alkane mixture to reach the purity of more than 95 HPLC area % of RSVLTBS and having less than 1 HPLC area % of RSVLTBS diastereoisomer impurity d) desilylating RSVLTBS to obtain crude RSVL e) treating RSVL by ethers to obtain crystalline product f) optionally recrystallising the obtained product to obtain RSVL of high purity (preferably having more than 97 HPLC area % of RSVL).

Preferably if the stationary phase is SiO$_2$ and the mobile phase is 1-20% n-butanol in n-heptane the step b) is omitted and crystalline RSVLTBS is precipitated from mobile phase by cooling to a temperature around −10 to +5° C.

The key intermediate compounds of formula RSVLTBS and RSVL can then be subjected to further synthesis steps in order to yield rosuvastatin or pharmaceutically acceptable salts thereof by synthesis routes known to or readily devisable by a person skilled in the art. As shown in the scheme below, following synthesis route may be applied:

rosuvastatin

For preparing a pharmaceutical composition comprising rosuvastatin or pharmaceutically acceptable salts thereof as active ingredient, first rosuvastatin or pharmaceutically acceptable salt thereof is provided by the process as described above.

Then, the thus prepared rosuvastatin or pharmaceutically acceptable salt thereof is suitably admixed with at least one suitable pharmaceutically acceptable excipient. Pharmaceutically acceptable excipients may be selected from the group consisting of binders, diluents, disintegrating agents, stabilizing agents, preservatives, lubricants, fragrances, flavoring agents, sweeteners and other excipients known in the field of the pharmaceutical technology. Preferably, excipients may be selected from the group consisting of lactose, microcrystalline cellulose, cellulose derivatives, e.g. hydroxypropylcellulose, polyacrylates, calcium carbonate, starch, colloidal silicone dioxide, sodium starch glycolate, talc, magnesium stearate, polyvinylpyrrolidone, polyethylene glycol and other excipients known in the field of the pharmaceutical technology.

EXPERIMENTAL PROCEDURES

Example 1

5-((E)-2-((2S,4R)-4-(tert-butyldimethylsilyloxy)-6-oxotetrahydro-2H-pyran-2-yl)vinyl)-4-(4-fluorophenyl)-6-isopropyl-2-(N-methylmethanesulfonylamino)pyrimidine (RSVLTBS)

-continued

RSVLTBS

To a stirred suspension of ((4-(4-fluorophenyl)-6-isopropyl-2-(N-methylmethylsulfonamido)pyrimidin-5-yl)methyl)tributylphosphonium 2,2,2-trifluoro-acetate (50.4, 77 mmol) at room temperature in dry toluene (800 mL) sodium hexamethyldisilazane (NaHDMS) in toluene (130 mL of 0.6 M, 77 mmol) was added portionwise in 10 minutes. The reaction mixture was stirred for 60 min and treated at room temperature with a solution of (2S,4R)-4-(tert-butyldimethylsilyloxy)-6-oxo-tetrahydro-2H-pyran-2-carbaldehyde (20 g, 77 mmol) in 2.5 L of dry toluene obtained by dissolution of (4R,6S)-4-(tert-butyldimethylsilyloxy)-6-(dihydroxymethyl)-tetrahydropyran-2-one (21.4 g, 77 mmol) in toluene and removal of released water. After 24 hours of stirring at room temperature the solution was treated with saturated ammonium chloride solution or water. The aqueous phase was extracted with methyl t-butyl ether (2×2 L), and the combined organic layers dried and concentrated to give oily residue with 25-40% HPLC area of RSVLTBS.

Preparation of Crystalline RSVLTBS

Example 2

Figure 1:
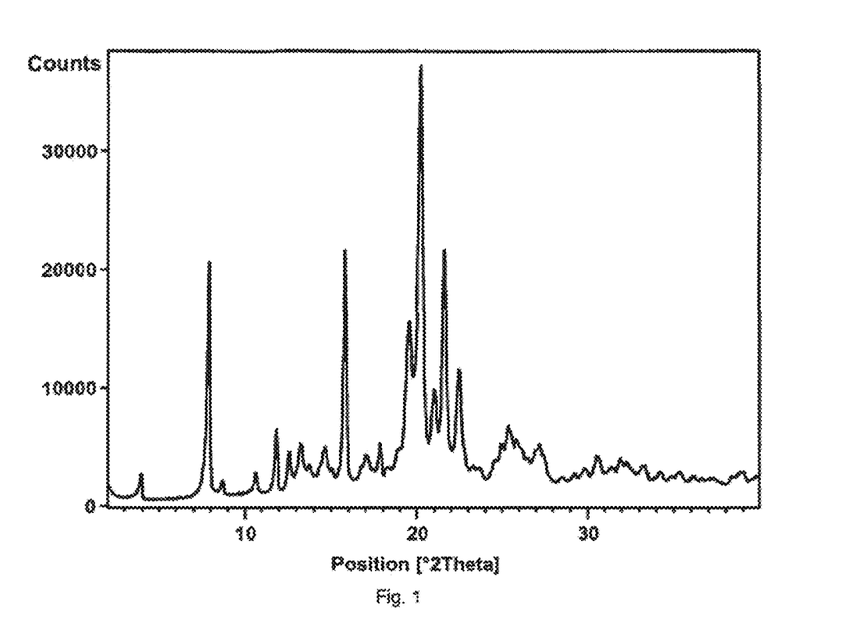
FIG. 1 shows an X-Ray powder diffractogram of crystalline RSVL according to present invention.
Figure 2:
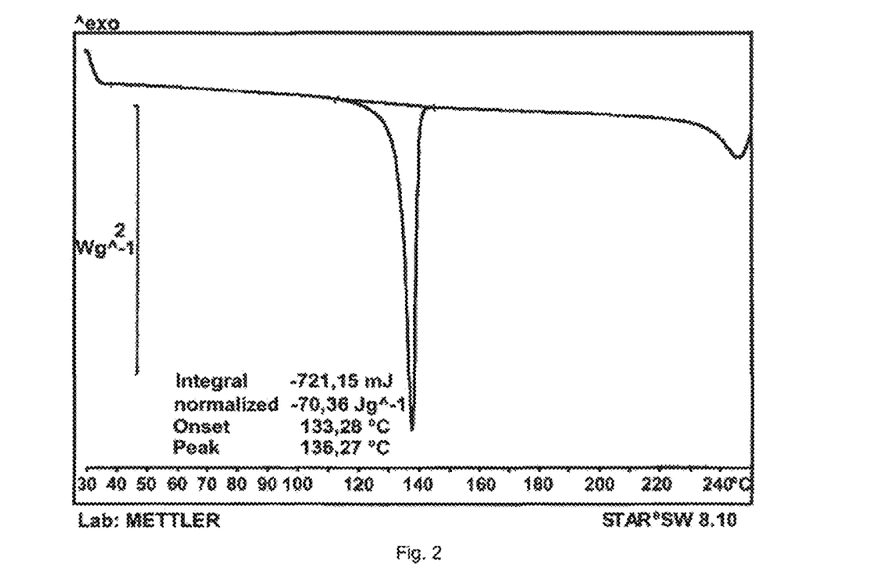
FIG. 2 shows a DSC curve of crystalline RSVL according to present invention.
Figure 3:
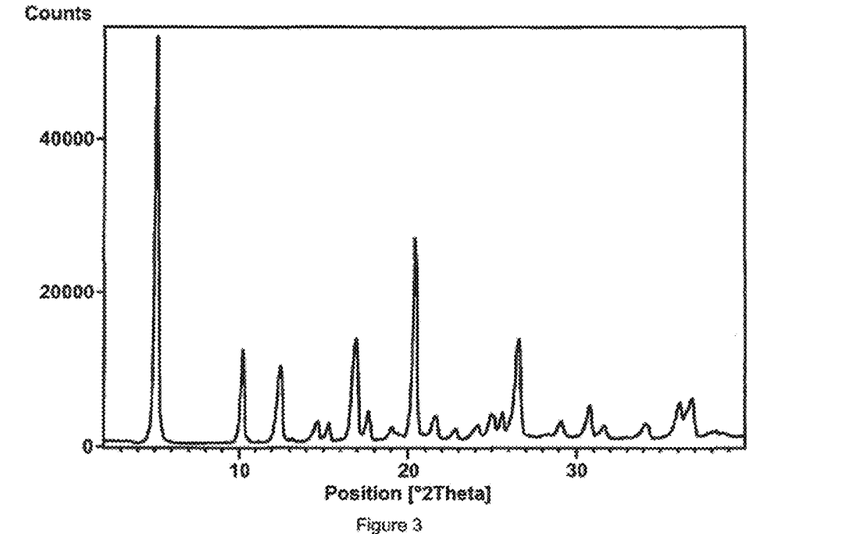
FIG. 3 shows an X-Ray powder diffractogram of crystalline RSVLTBS Form I according to present invention.
Figure 4:
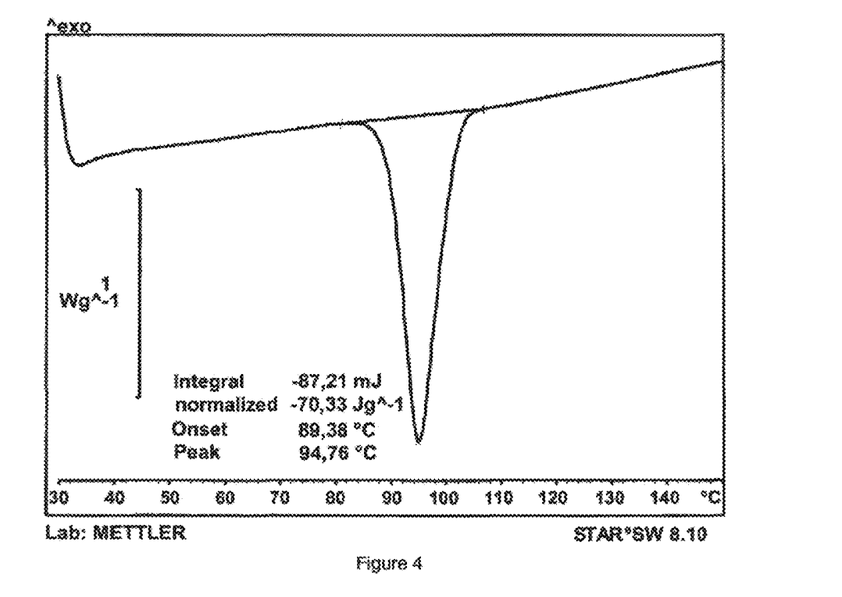
FIG. 4 shows a DSC curve of crystalline RSVLTBS Form I according to present invention.

Crude oil (HPLC: 33.0% area RSVLTBS) as obtained in Example 1 was diluted in a solvent at 50° C., which contained 2 vol. % of n-BuOH in n-heptane (20 mg/ml). Milky solution was filtered through 0.2 μm PTFE (polytetrafluoroethylene) filter and RSVLTBS crystallised from clear, saturated solution by cooling the solution down to 4° C. in darkness. Yield was 50-70%. Thus obtained crystalline RSVLTBS Form I is of enhanced purity (HPLC: 68 HPLC area % and higher RSVLTBS; 16 area % RSVLTBS diastereoisomer; 6 area % Z-epimer of RSV-L-TBS). X-Ray and DSC shows form I as depicted in FIGS. 3 and 4.

Example 3

Figure 5:
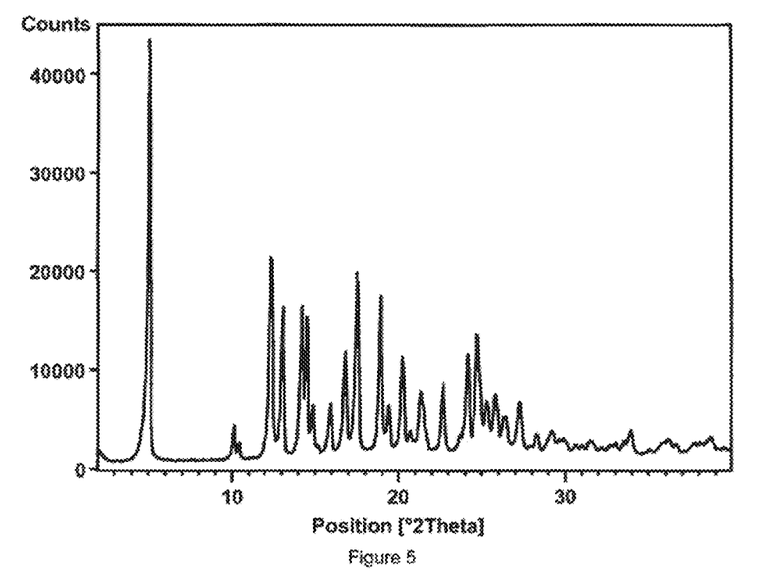
FIG. 5 shows an X-Ray powder diffractogram of crystalline RSVLTBS Form II according to present invention.
Figure 6:
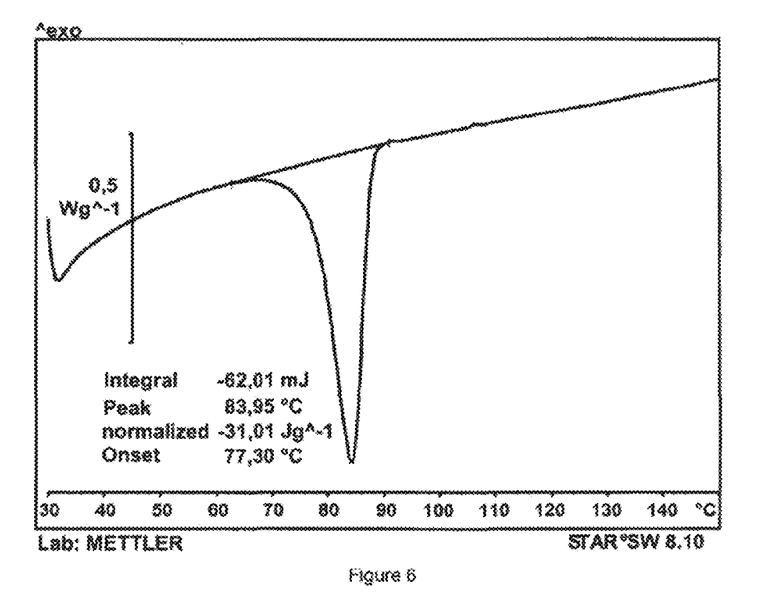
FIG. 6 shows a DSC curve of crystalline RSVLTBS Form II according to present invention.
Figure 7:
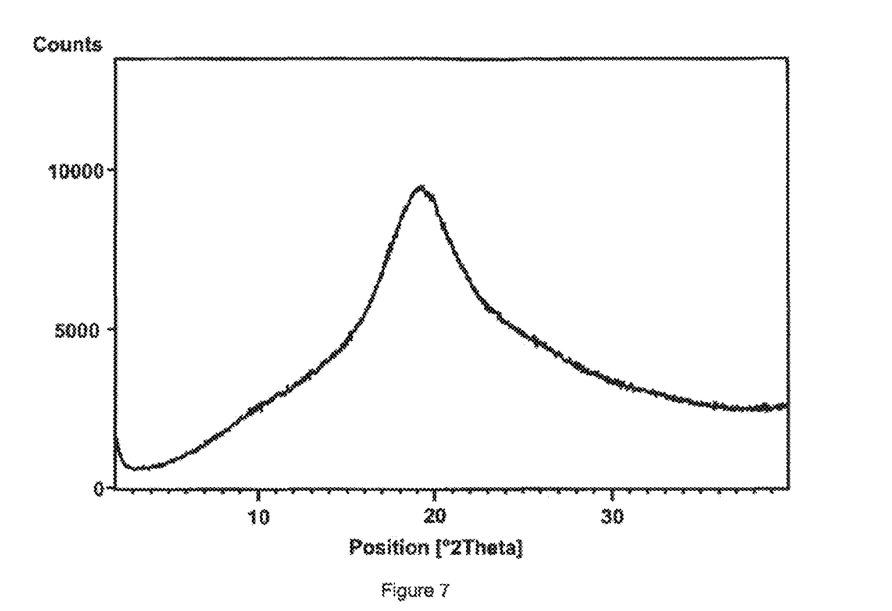
FIG. 7 shows an X-Ray powder diffractogram of amorphous RSVL according to present invention

Crude RSVLTBS (35.0 g, HPLC: 65.0% area RSVLTBS, 19.4% area diastero RSVLTBS) was dissolved in 35 mL n-butanol at 90° C. The hot solution was cooled to 80° C. and 100 mL of n-hexane was added. Then, the obtained mixture was cooled to −5° C. and was stirred for 1.5 hours. Precipitated crystals of the product were collected by filtration, washed with 20 mL of hexane and dried to give 21.71 g (yield 70.9%, assay 74.34%) of RSVLTB Form II crystals (HPLC: 89.48 area % RSVLTBS; 8.87 area % RSVLTBS diastereoisomer). X-Ray and DSC shows form II as depicted in FIGS. 5 and 6.

Purification of RSVLTBS Using HPLC

Example 4

NP isocratic HPLC-UV preparative chromatography: Kromasil 60-5DIOL, 250×4.6 mm, 10 μm Analytical Conditions:
V inj: 10 μl
$\lambda_{analytical}$: 242 nm
Flow: 0.8 ml/min
T column: 10° C.
Cvz≈100 mg/ml
$C_{RSV-L-TBS}$≈30 mg/ml
MP: 980 ml heptane+20 ml EtOH+0.2 ml $H_2O$
solvent: n-heptan:AcOEt c=70:30
Loading: ≈6 mg/cm$^2$
Preparative Conditions:
V inj: 10 ml
λ: 300 nm
Flow: 118 ml/min
$T_{Mobile\ phase}$: 10° C.
$C_{sample}$≈365 mg/ml
$C_{RSV-L-TBS}$≈80 mg/ml
MP: 980 ml heptane+20 ml EtOH+0.2 ml $H_2O$
solvent: heptan:AcOEt=70:30
Loading: ≈20 mg/cm$^2$ DIOL stationary phase in the combination with mobile phases constituted from n-hexane and/or n-heptane:alcohols (n=2-12): water in ratios from 99.5%-86% of hexane/heptane:0.5%-14% of alcohols:0-1% of water (m/m/m) were found to be suitable for preparative RSVLTBS cleaning. The preparative cleaning was performed with linear flow velocities ranged between 3-18 cm/min, temperature range 4-40° C., and loadings ranged between 20-500 mg of crude RSVLTBS/cm$^2$, solvent was 10 to 90 vol. % mixture of ethyl acetate in n-heptane. Evaporation was performed in vacuum (200-5 mbar) and in darkness at temperatures from 0-80° C. Yield was 70-80%. An oily sample of 54.34 HPLC area % was purified to oily product of 87.73 HPLC area % which may be further crystallised as described in Example 3 to give a product with purity of >95 HPLC area %.

Example 5

NP isocratic HPLC-UV preparative chromatography: Kromasil 100-10SIL; 250×4.6 mm10 μm;
Analytical Conditions:
V inj: 2 μl
$\lambda_{analytical}$: 242 nm
Flow: 0.8 ml/min
T kolone: 10° C.
$C_{sample}$≈300 mg/ml
$C_{RSV-L-TBS}$≈100 mg/ml
MF: 975 ml heptan+25 ml n-BuOH
solvent: n-heptan:AcOEt=70:30
Loading≈4 mg/cm$^2$
Preparative Conditions:
V inj: 20 ml
λ: 300 nm
Flow: 118 ml/min
$T_{Mobile\ phase}$: 10° C.
$C_{sample}$≈150 mg/ml
$C_{RSV-L-TBS}$≈40 mg/ml
MP: 980 ml heptane+25 ml EtOH
Solvent: n-heptane:AcOEt=70:30
Loading≈75 mg/ml $SiO_2$ stationary phase in the combination with mobile phases constituted by (n-hexane and/or n-heptane:alcohols (n=2-12) in ratios from 99.5 hexane/heptane:0.5%-10% of alcohol (V/V) were found to be suitable for preparative RSVLTBS purification. The preparative purification was performed with linear flow velocities ranged between 3-18 cm/min, temperature range 4-40° C., and loadings ranged between 20-500 mg of crude RSVLTBS/cm², solvent was 10 to 90 vol. % mixture of ethyl acetate in n-heptane. Evaporation was performed in vacuum (200-5 mbar) and darkness at temperatures from 0-80° C. RSVLTBS preparative cleaning was performed on SiO₂ stationary phase with 1-4 vol. % n-butanol in n-heptane mobile phase. The crystals were obtained from the mobile phase fractions when cooled over night down to 4° C. in the darkness. To enhance yield of crystallisation the mother liquor was evaporated in a cool and dark place in order to decrease the content of n-butanol in n-heptane down to 0.1%. Yield was 70-80%. Crystalline product obtained was of good purity (91.0 HPLC area %) and may be further recrystallised as described in Example 3 to give a product with purity of >95 HPLC area %.

Preparation of Crude Rosuvastatin Lactone (RSVL)

Example 6

To a solution of tetrabutylammonium fluoride trihydrat (75.77 g) and acetic acid (89 mL) in 5 L of tetrahydrofuran solution of RSVLTBS (98.0 g) (HPLC area: 97.3%) in tetrahydrofuran (400 mL) was added. The reaction mixture was stirred at 40° C. for 21 hours. The tetrahydrofuran was evaporated to afford 201 g of yellow oily product.

Example 7

To a solution of tetrabutylammonium fluoride trihydrat (46.0 g) and acetic acid (54.5 mL) in 2.5 L of tetrahydrofuran was added RSVLTBS (60 g) (HPLC assay: 97.69%). The reaction mixture was stirred at 40° C. for 20 hours. The tetrahydrofuran was evaporated to afford 110 g of yellow oily product. The oily product was dissolved in 300 mL ethyl acetate. The organic solution was washed four times with 200 mL of saturated water solution of NaHCO₃ and twice with 200 mL of water. The organic phase was evaporated to give a colorless oily product. The yield was 55.56 g (yield ca. 82% based on HPLC assay). HPLC: 70.9 area % RSVL.

The obtained crude RSVL product was divided in several portions and subjected to crystallisation and amorphisation experiments as described below:

Preparation of Crystalline RSVL from Oily Material

Example 8

A 13.75 g of crude product RSVL as obtained in example 7 was dissolved in 21 mL of acetone. 265 mL of water was added to the solution. Mixture was stirred for 48 hours at 25° C. The white crystalline product was filtered off and dried under vacuum at 40° C. to give a 8.10 g, white crystalline powder (yield 58.9% based on mass/69.3% based on HPLC assay).

HPLC: 83.21 area % RSVL

Example 9

A 13.75 g of crude product RSVL as obtained in example 7 was dissolved in 20 mL of tetrahydrofurane. 303 mL of water was added to the solution. Mixture was stirred for 48 hours at 25° C. The white crystalline product was filtered off and dried under vacuum at 40° C. to give white crystalline powder (yield 8.66 g, 63% based on mass/80% based on HPLC assay).

HPLC: 90.62 area % RSVL

Example 10

A 206 mL of water was added to 13.75 g of crude RSVL product as obtained in example 7. The mixture was stirred for 5 days at 25° C. The white crystalline product was filtered off and dried under vacuum at 40° C. to give a white crystalline powder (yield 8.04 g, 58.5% based on mass/57.8% based on HPLC assay).

HPLC: 70.34 area % RSVL

Purification of Crude Crystalline RSVL

Crystalline crude RSVL product can be purified by extraction from ether, preferably methyl t-butyl ether.

Example 11

The oily product was dissolved in 1 L methyl t-butyl ether. The organic solution was washed four times with 750 mL of saturated water solution of NaHCO₃ and twice with 600 mL of water. The organic phase was evaporated to give a white crystalline product. The yield was 67.9 g of RSVL (yield 86.3% based on HPLC assay). HPLC: 97.3 area % RSVL.

Crystalline crude RSVL product can be further purified by recrystallisation from ethanol, 2-propanol or ethyl acetate:

Example 12

Crude RSVL (2.00 g) as obtained in example 8 (HPLC area %: 83.21) was recrystallised from 8 mL of ethanol. The white crystalline product was filtered off and dried under vacuum at 40° C. to give 1.73 g (86.5% yield based on mass) of RSVL. HPLC: 98.3 area % RSVL Example 13

Crude RSVL (2.00 g) as obtained in example 8 was (HPLC area %: 83.21) recrystallised from 8 mL of 2-propanol. The white crystalline product was filtered off and dried under vacuum at 40° C. to give 1.80 g (90% yield based on mass) of RSVL. HPLC: 98.0 area % RSVL Example 14

Crude RSVL (2.00 g) as obtained in example 8 was recrystallised from 8 mL of ethyl acetate. The white crystalline product was filtered off and dried under vacuum at 40° C. to give 1.43 g (71.5% yield based on mass) of RSVL. HPLC: 98.6 area % RSVL.

Examples 15-17

Crude RSVL (10.00 g) as obtained in example 11 was recrystallised from 40 mL of ethanol, 2-propanol or ethyl acetate. The white crystalline product was filtered off and dried under vacuum at 40° C. to give purified RSVL. The results are presented in the table:

| Crude RSVL as obtained in Example 11 HPLC area %: 97.3% | Solvent | Volume of solvent [mL] | Product yield based on mass | HPLC area % RSVL |
|---|---|---|---|---|
| 10 g | EtOH | 40 | 8.98 g (89.8%) | 97.6 |
| 10 g | iPrOH | 40 | 9.22 g (92.2%) | 97.4 |
| 10 g | AcOEt | 40 | 7.10 g (71.0%) | 97.9 |

Consecutive Crystallisation of RSVL from Reaction Product

Example 18

To a solution of tetrabutylammonium fluoride trihydrate (9.57 g) and acetic acid (4.75 mL) in 86 mL of tetrahydrofuran was added RSVLTBS (12.92 g=10.00 g pure RSVLTBS) (HPLC assay 77.4%; HPLC 85.38 area % RSVLTBS, 8.21 area % RSVLTBS diastereoisomer). The reaction mixture was stirred at 23° C. for 24 hours. The tetrahydrofuran was evaporated. The oily product was dissolved in 200 mL methyl t-butyl ether. The organic solution was washed four times with 75 mL of saturated water solution of NaHCO$_3$ and three times with 75 mL of water. The organic phase was stirred for 16 hours at 24° C. White solid product was filtered off, washed with 20 mL of methyl t-butyl ether and dried to give 5.68 g of RSVL (yield 70.82%) (HPLC: 94.05 area % RSVL, 2.65 area % RSVL diastereoisomer, 0.28 area % RSVLTBS) Above prepared RSVL (4.00 g) was dissolved in 16 mL of 2-propanol at reflux temperature. The solution was cooled down to 0° C. and stirred at 0° C. for one hour. The white crystalline product was filtered off and dried. The yield was 3.55 g (yield: 88.75%, HPLC: 94.94 area % RSVL, 1.57 area % RSVL diastereoisomer, 0.22 area % RSVLTBS)

Amorphous RSVL

Amorphous RSVL can be prepared from dry alcohol (MeOH, EtOH, iPrOH), ester (AcOEt, tBuOAc) or ether (THF, MTBE) solution of RSVL in Spray Dryer at 70-90° C. in hot nitrogen atmosphere:

Example 19

200 mL of ethyl acetate solution of RSVL (concentration is 40 g/L) was laid on mini spray dryer Büchi B 290. Temperature of nitrogen gas flow was set to 70° C. The obtained solid product was collected and dried in vacuum at 45° C. to give 7.6 g (95% yield) of amorphous RSVL as white powder (FIG. 8).

The products were analyzed by following methods:
X-Ray Powder Diffraction Method:
Conditions for obtaining powder X-ray diffraction (XRD) patterns: The powder X-ray diffraction patterns were obtained by methods known in the art using Philips X'Pert PRO diffractometer with X'Celerator detector using CuKα radiation (tube operating at 45 kV and 40 mA) in the Bragg-Brentano (reflection) geometry. Data were recorded from 2 to 40 °2θ in steps of 0.033 °2θ and the measurement time of 50 seconds per step. Variable divergence and antiscatter slits were used to maintain 12 mm of sample length irradiated.
Differential Scanning Calorimetry:
Conditions for obtaining DSC thermograms: Thermograms were obtained with Mettler Toledo DSC822e differential scanning calorimeter. The sample (4-6 mg) was placed in an unsealed aluminium pan with a hole and heated at 5° C./min in the temperature range from 30° C. to 250° C.

The invention claimed is:
1. A process for preparing the compound of formula RSVL comprising the steps of:
providing a compound of formula RSVLTBS:

converting the compound of formula RSVLTBS into the compound of formula RSVL by removal of silyl protection group in the presence of tetrabutyl ammonium fluoride and acid in organic solvent, and isolating said compound of formula RSVL,
further purifying RSVL by extraction with methyl t-butyl ether and forming crystallized RSVL; and recrystallizing the crystallized RSVL using a solvent selected from a group consisting of ethanol, 2-propanol and ethyl acetate and forming recrystallized RSVL.

2. The process according to claim 1, wherein said RSV-LTBS is in crystalline form.

3. A process for the preparation of rosuvastatin or pharmaceutically acceptable salt thereof, comprising the steps of:

a) carrying out a process for preparing the compound of formula RSVL according to claim 1, and b) subjecting the thus prepared compound of formula RSVL to further synthesis steps to yield rosuvastatin or pharmaceutically acceptable salts thereof.

4. A process for the preparation of a pharmaceutical composition comprising rosuvastatin as active ingredient, comprising the steps of:

a) preparing rosuvastatin or pharmaceutically acceptable salts thereof according to the process according to claim 3, and b) admixing the thus prepared rosuvastatin or pharmaceutically acceptable salt thereof with at least one pharmaceutically acceptable excipient.

5. The process according to claim 1, wherein the RSV-LTBS comprises a crystalline form selected from a group consisting of:

a) Form I, characterized by XRD pattern having any 6 peaks at 2θ values selected from the group consisting of: 5.1, 10.2, 12.5, 14.7, 15.3, 17.0, 17.7, 20.4, 26.6 and 30.8, respectively exactly or ±0.2 degrees 2θ at the indicated 2θ values or by having a melting point falling in a range of 85-105° C.; and b) Form II, characterized by XRD pattern having any 6 peaks at 2θ values selected from the group consisting of 5.1, 12.4, 13.1, 14.3, 17.6, 18.9, 22.7, 24.2, 24.8 and 25.0, respectively exactly or ±0.2 degrees 2θ at the indicated 2θ values or by having a melting point falling in a range of 70-92° C.

6. The method according to claim 1, comprising, after further purifying the RSVL by extraction with methyl t-butyl ether, the step of washing the further purified RSVL with water.

* * * * *